United States Patent [19]

Froning et al.

[11] Patent Number: 4,543,091
[45] Date of Patent: Sep. 24, 1985

[54] X-RAY MARKER DEVICE

[75] Inventors: Edward C. Froning, P.O. Box 1768, Rancho Santa Fe, Calif. 92067; Gregory S. Graham, Ventura, Calif.

[73] Assignee: Edward C. Froning, Rancho Sante Fe, Calif.

[21] Appl. No.: 495,665

[22] Filed: May 18, 1983

[51] Int. Cl.[4] ............................................. A61B 6/12
[52] U.S. Cl. .............................. 604/116; 248/297.5; 378/163; 403/374
[58] Field of Search ............. 128/1 R, 303 B; 604/51, 604/116; 378/162–165; 350/248, 245; 351/57; 248/297.5; 403/374

[56] References Cited

U.S. PATENT DOCUMENTS

| | | | |
|---|---|---|---|
| 1,276,501 | 8/1918 | Douglas | 248/297.5 |
| 1,370,640 | 3/1921 | Granger | 378/163 |
| 2,765,136 | 10/1956 | Knapp | 403/374 |
| 3,297,291 | 1/1967 | Everett | 350/245 |
| 3,577,160 | 5/1971 | White | 378/163 |
| 3,619,611 | 11/1971 | Hall | 378/165 |
| 3,770,956 | 11/1973 | Johnson | 378/164 |
| 3,941,127 | 3/1976 | Froning | 604/51 |
| 3,955,884 | 5/1976 | Del Pesco, Sr. | 350/248 |
| 4,187,423 | 2/1978 | Ehrhardt | 378/164 |
| 4,259,585 | 3/1981 | Novak et al. | 378/162 |
| 4,373,789 | 2/1983 | Roberts | 351/57 |
| 4,421,108 | 12/1983 | Cabrera et al. | 128/303 B |

FOREIGN PATENT DOCUMENTS

| | | | |
|---|---|---|---|
| 0836390 | 4/1952 | Fed. Rep. of Germany | 378/163 |
| 0385442 | 3/1965 | Fed. Rep. of Germany | 248/297.5 |
| 0205217 | 11/1967 | U.S.S.R. | 378/163 |

Primary Examiner—C. Fred Rosenbaum
Assistant Examiner—Michelle Lester
Attorney, Agent, or Firm—Julian Caplan

[57] ABSTRACT

For pre-operative radiography preparatory to stereotaxic lateral extradural disc puncture (e.g. as disclosed in U.S. Pat. No. 3,941,127) the patient is placed on his side and a radiographic film is exposed from which the surgeon calculates position and angle of needle approach to the disc before the actual operation begins. An X-ray opaque marker device similar to a ruler is located parallel and adjacent to the patient at the level of the midsaggital plane. Markings and numbers on the marker device show on the exposed film. With prolonged X-ray exposure, the image of the marker may be "burned". The present device provides a series of radiopaque shields which may be interposed between the marker and the film to reduce burn-out of the image of the marker on the film. A convenient stand supports and stores the marker and one or more shields so that they may be individually and selectively raised and turned into operative position.

4 Claims, 4 Drawing Figures

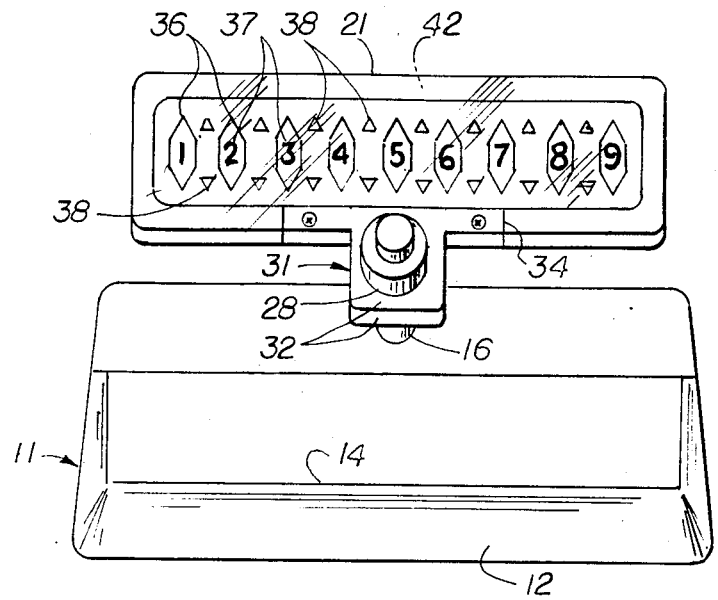
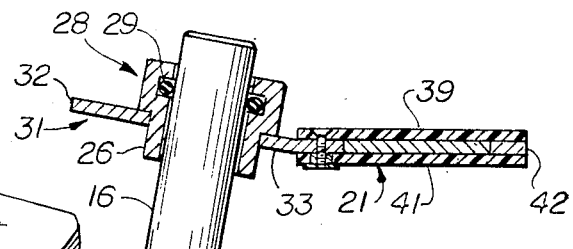
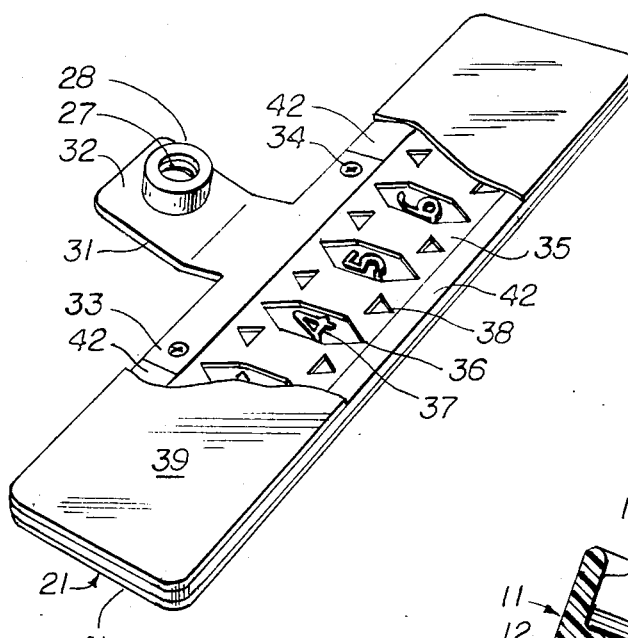
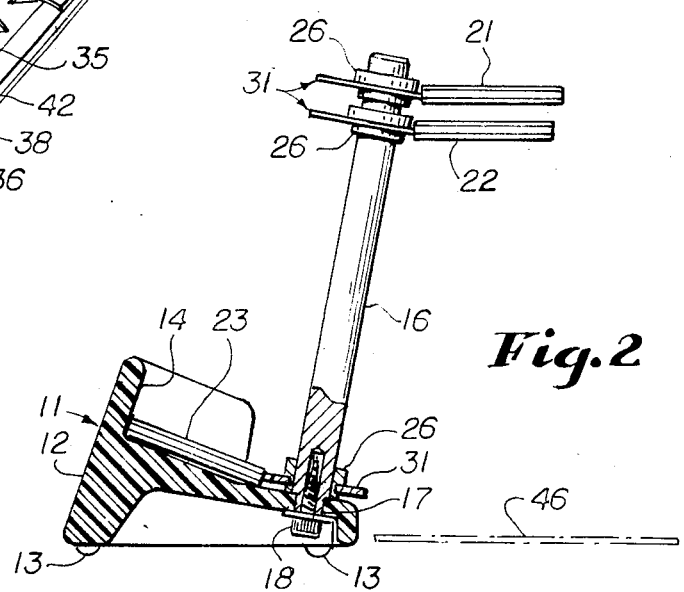
Fig. 1
Fig. 3
Fig. 4
Fig. 2

X-RAY MARKER DEVICE

This invention relates to a new and improved X-ray marker device and constitutes an improvement upon U.S. Pat. No. 3,941,127. The use of such a marker is described in said patent, particularly at column 3, lines 30–63.

In accordance with the present invention, a marker is provided which is substantially X-ray opaque consisting of three laminations. The middle lamination is cut away to provide markers and numerals which appear on the X-ray film and are subsequently used by the surgeon in planning the operation. It has been found that X-ray exposure tends to "burn" the images of the markings so that they are not legible on the film. The present invention provides a means selectively for increasing the amount of shielding of the marker to prevent burn-out. Thus, one or more radiopaque shields may selectively be positioned in proximity to the marker to reduce burn-out of the images.

A plurality of shields, each individually movable into position is preferred so that the desired degree of radiopaqueness may be selected, depending upon the duration and intensity of X-ray exposure.

One of the features of the invention is a provision of a stand having a base located out of the field of X-ray exposure in which the marker and shields may be stored when they are not in use. Extending at an angle from the base toward the patient is a rod. By raising the marker along the rod to a stop located at its upper extremity and turning the marker 180°, the marker may be raised from its storage position to its position of use. Furthermore, one or more shields may also be moved along the rod and turned 180° thereby coming into position below the marker.

A feature of the invention is the fact that the marker and shields may be conveniently manipulated by the surgeon with a minimum of effort and concentration required.

Once the marker or shield is raised into position on the rod, it is held by friction until it is necessary to lower the device into its storage position.

Since the rod is slanted toward the patient, the stand serves as a weight to prevent the rod and devices held thereby from tilting.

Another feature of the invention is the fact that the entire device may be cleaned.

Other objects of the present invention will bcome apparent upon reading the following specification and referring to the accompanying drawings in which similar characters of reference represent corresponding parts in each of the several views.

In the drawings:

FIG. 1 is a top plan view of the device in position of use.

FIG. 2 is a side elevational view partially broken away in section to reveal internal construction.

FIG. 3 is an enlarged fragmentary sectional view of the marker and upper end of the rod.

FIG. 4 is an exploded perspective view of a portion of the shield and associated structure.

Stand 11 has a base 12 formed of a material such as stainless steel, aluminum, or other suitable material, and having sufficient mass to prevent the stand from tilting. Base 12 is supported by feet 13 on a radiotransparent table (not shown) on which the patient rests during the exposure to X-rays. The top of base 12 is formed with a storage depression 14 of sufficient size to store the markers and shields hereinafter described. Extending upwardly at an angle of about 10° to the vertical is a smooth polished rod 16 which extends away from the storage depression 14. The lower end of rod 16 is formed with a reduced diameter. portion 17 which fits through a hole in the base 12 and is secured by a screw 18, or other convenient means.

Slidable on and rotatable about rod 16 are a marker 21 and one or more shields 22. In the drawings a top shield 22 and a lower shield 23 are illustrated, but fewer or more shields may be supplied. Associated with marker 21 and each shield 22, 23 is a collar 26 which slides over the rod 16 and is provided with a top flange 28 suitably grooved to receive on its interior O-ring 27. Friction, particularly of the O-ring 27, tends to bind the collar 26 against sliding down the rod 16 so that once the marker 21 or one of the shields is in place, it tends to remain there until positively lowered by the surgeon or attendant.

Forcefit to engage collar 26 is a manipulator 31 having a finger grip 32 on one side of the rod 16 and an extension 33 on the other.

Directing attention now to FIGS. 1, 3, and 4 marker 21 has a middle lamination 35 of a radiopaque material such as lead. A series of diamond-shaped cutouts 36 are formed in lamination 35 spaced equidistantly along the length of the middle lamination 35 and in the center of each cutout 36 is a numeral 37. Also cut out in lamination 35 are points 38 spaced midway between cutouts 36. Since the marker 21 is raised on the rod 16 so that it is in a horizontal plane which includes the midsaggital plane of the spine of the patient, an image of the cutouts 36, numerals 37 and points 38 will be exposed on the X-ray film 46 at dimensions proportionate to the dimension of the marker 21 and proportional to the actual dimensions of the physical details of the spine of the patient. Middle lamination 35 is encased between top lamination 39 and bottom lamination 41 which comprise a frame for the marker 21. Bottom lamination 41 has a peripheral raised rim 42 dimensioned to receive middle lamination 35. Top lamination 39 fits over rim 42 and middle lamination 35. Laminations 39 and 41 may be of black acrylic or other partially radiopaque material.

Rim 42 is interrupted in an opening 43 to receive extension 33. Retainer screws 34 extend through holes in extension 33 and are threaded into lower lamination 41.

The shields 22, 23 also have manipulators 31 and similarly attached to extensions 33 thereof (not shown).

In use, initially the marker 21 and the shields 22, 23 therebelow are stored in the storage compartment 14 of the stand 11. Base 12 is positioned on the radiotransparent operating table adjacent, but preferably removed from, the edge of the film 46. The surgeon or assistant grasps the finger grip 32 of the marker 21 and raises the collar 26 partially up the rod 16 and then turns the marker 21 from storage position shown in FIG. 2 until the marker is in the midsaggital plane of the patient. Because of the weight of the marker 21, the collar 26 and particularly the O-ring 27 tend to securely engage the surface of the rod 16, holding the marker 21 in desired position. Shield 22, if required, may be raised into position immediately below the marker 21 as may the shield 23. After the film 46 has been exposed, the shields and marker may be returned to storage position.

What is claimed is:

1. An X-ray marker device comprising a base formed with a rectangular storage depression, a single, round rod extending upward from said base adjacent one longitudinal edge of said depression, a substantially rectangular marker shaped to fit into said depression, said marker having a cylindrical collar fixed thereto, said collar being rotatable relative to said rod and longitudinally slidable along said rod between a storage position with said marker stored in said depression and an operative position, said marker when in operative position being on the side of said rod opposite said depression, and turned 180° relative to its storage position and substantially elevated above said base, said collar having friction means on its interior, the weight of said marker causing said friction means to secure said collar and said marker against movement longitudinally of said rod; said marker being laminated, one lamina being of radiopaque material formed with cut-outs pointed at at least one end and radiopaque numerals located in said cut-outs.

2. A device according to claim 1 in which said rod slants away from said base.

3. A device according to claim 1 in which said collar has a finger grip fixed to said collar extending in a second direction from said rod and means securing said extension to said marker.

4. A device according to claim 1 which further comprises at least one radiopaque shield of approximately the same length and width as said marker; said shield being slidable along said rod independently of said marker from a lowered position to a raised selected position of adjustment.

* * * * *